United States Patent
Somasundaram

(10) Patent No.: US 6,857,147 B2
(45) Date of Patent: *Feb. 22, 2005

(54) SYNCHRONIZATION DRIVE FOR A LONGITUDINAL AXIS TELESCOPIC GUIDANCE MECHANISM

(75) Inventor: Baskar Somasundaram, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/379,138

(22) Filed: Mar. 4, 2003

(65) Prior Publication Data

US 2004/0172756 A1 Sep. 9, 2004

(51) Int. Cl.[7] .................................................. A47B 7/02
(52) U.S. Cl. ............................................. 5/601; 5/600
(58) Field of Search .......................... 5/601, 607, 608, 5/610, 611, 600

(56) References Cited

U.S. PATENT DOCUMENTS

| | | | |
|---|---|---|---|
| 4,541,108 A | 9/1985 | Grady et al. | |
| 4,715,591 A | 12/1987 | Dragmen | |
| 4,761,000 A | 8/1988 | Fisher et al. | |
| 4,769,584 A | 9/1988 | Irigoyen et al. | |
| 4,912,754 A | 3/1990 | Van Steenburg | |
| 5,048,071 A | 9/1991 | Van Steenburg | |
| 5,156,166 A | 10/1992 | Sebring | |
| 5,205,004 A | 4/1993 | Hayes et al. | |
| 5,572,569 A | 11/1996 | Benoit et al. | |
| 6,038,718 A | 3/2000 | Pennington et al. | |
| 6,269,499 B1 | 8/2001 | Amir | |
| 6,353,949 B1 | 3/2002 | Falbo | |
| 6,615,428 B1 * | 9/2003 | Pattee | 5/601 |
| 6,651,279 B1 * | 11/2003 | Muthuvelan | 5/600 |

FOREIGN PATENT DOCUMENTS

DE 268 555 B1 10/1986

\* cited by examiner

Primary Examiner—Michael F. Trettel
Assistant Examiner—Fredrick Conley
(74) Attorney, Agent, or Firm—McAndrew, Held & Malloy, Ltd.; Peter J. Vogel; Michael A. Dellepenna

(57) ABSTRACT

Certain embodiments include a system and method for synchronized telescopic guidance along a longitudinal axis in a patient positioning system. The system includes a top channel driven by a motor, a bottom channel synchronized with the top channel, and a rack and pinion for transmitting drive from the top channel to the bottom channel. The bottom channel is driven by the top channel. The system may also include a gear for transmitting drive from the top channel to the bottom channel using the rack and pinion. The system may also include a plurality of racks and pinions for transmitting drive from the top channel to the bottom channel. Additionally, the size of the pinion meshing with the top channel may be half the size of the pinion meshing with the bottom channel. The bottom channel may move along the top channel.

20 Claims, 7 Drawing Sheets

Up-Down & Rotation (Patient Loading)

Longitudinal Travel (Scanning)

Longitudinal Tilt (Vascular Tilt)

Longitudinal Axis

Head Up tilt (Positive)

Head Down tilt (Negative)

HEAD - DOWN TILT

HEAD - UP TILT

ISO-CENTER TRACKING

700

SYNCHRONIZATION DRIVE FOR A LONGITUDINAL AXIS TELESCOPIC GUIDANCE MECHANISM

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to longitudinal motion in a patient positioning system. In particular, the present invention relates to synchronized drive for a telescopic guidance mechanism along a longitudinal axis in a patient positioning system.

Patient positioning platforms allow a medical practitioner, such as a doctor, nurse or technician, to position a patient during a medical procedure, such as XR, CT, EBT, nuclear, and PET procedures. Patient positioning platforms, such as tables or other supports, allow a patient to be elevated, moved in lateral and longitudinal directions, rotated and/or tilted during a procedure. Patient positioning platforms improve a medical practitioner's ability to examine and/or perform a medical procedure on a patient.

There is a need for an improved patient positioning platform that may be used in angiography, neurology, and cardiac procedures. Current patient positioning platforms may introduce limitations in obtaining images of blood flow in arteries, heart, lungs, or brain, for example. Thus, a patient positioning system that improves stability and reliable positioning for blood flow imaging in angiography, neurology, cardiac and other such procedures would be highly desirable. Additionally, a patient positioning system that provides reliable and easy positioning of a patient with flexibility to accommodate a variety of medical procedures and emergencies would be highly desirable.

An improved patient positioning platform is capable of performing complex motions to position a patient. During such complex motions, portions of the patient positioning platform may move downward due to gravity and lack of proper support. Lack of proper support or guidance of components in the patient positioning platform may produce unwanted movement in the patient positioning platform. Movement in the patient positioning platform may cause a collision with an object, such as the floor or other parts of a medical imaging system, and/or may shock or injure the patient. Additionally, unwanted movement of the patient positioning platform may disrupt system calibration and result in faulty measurements or image scans.

Current patient positioning systems include inadequate support for movement of the patient positioning platform. Portions of the patient positioning platform may overhang without support during movement. A patient positioning system with adequate support for the patient positioning platform during movement would be highly desirable.

Thus, a need exists for a method and system for synchronized drive for telescopic guidance along a longitudinal axis in a patient positioning system.

BRIEF SUMMARY OF THE INVENTION

Certain embodiments include a system and method for synchronized drive for a telescopic guidance mechanism along a longitudinal axis in a patient positioning system. The system includes a patient positioning surface for supporting a patient, a lift subsystem for adjusting elevation of the patient positioning surface, a tilt subsystem for tilting the patient positioning surface, and a longitudinal subsystem for moving the patient positioning surface in a longitudinal direction. The longitudinal system includes a first stage and a second stage. The second stage is driven in synchronization with the first stage to move the patient positioning surface in a longitudinal direction. The system also includes a position sensor for determining a position of the patient positioning surface and a control subsystem for controlling operation of the patient positioning system.

The system may also include a lateral subsystem for moving the patient positioning surface in a lateral direction and/or a rotation subsystem for rotating the patient positioning surface. Additionally, the system may include at least one brake to halt motion of the patient positioning surface.

The longitudinal system may include a rack and pinion system to drive the first and second stages. Also, gear ratios may be used between rack and pinion drives for the first and second stages to position the patient positioning surface. Additionally, the longitudinal system may allow manual movement of the patient positioning surface.

The method includes driving a first stage, transmitting drive from the first stage to a second stage, and moving a patient positioning platform in a longitudinal direction using drive from the synchronized first stage and second stage. A gear and drive system may drive the first stage. A rack and pinion system may transmit drive from the first stage to the second stage.

The method may also include moving the patient positioning surface to a desired position. Additionally, the method may include measuring the current position of the patient positioning surface using a position sensor. Furthermore, the method may include adjusting gear ratios between rack and pinion systems of the first stage and the second stage to position the patient positioning surface.

An embodiment of a synchronization drive system for a longitudinal axis telescopic guidance mechanism includes a top channel driven by a motor, a bottom channel synchronized with the top channel, and a rack and pinion for transmitting drive from the top channel to the bottom channel. The bottom channel is driven by the top channel. The system may also include a gear for transmitting drive from the top channel to the bottom channel using the rack and pinion. The system may also include a plurality of racks and pinions for transmitting drive from the top channel to the bottom channel. Additionally, the size of the pinion meshing with the top channel may be half the size of the pinion meshing with the bottom channel. The bottom channel may move along the top channel.

Figure 1:
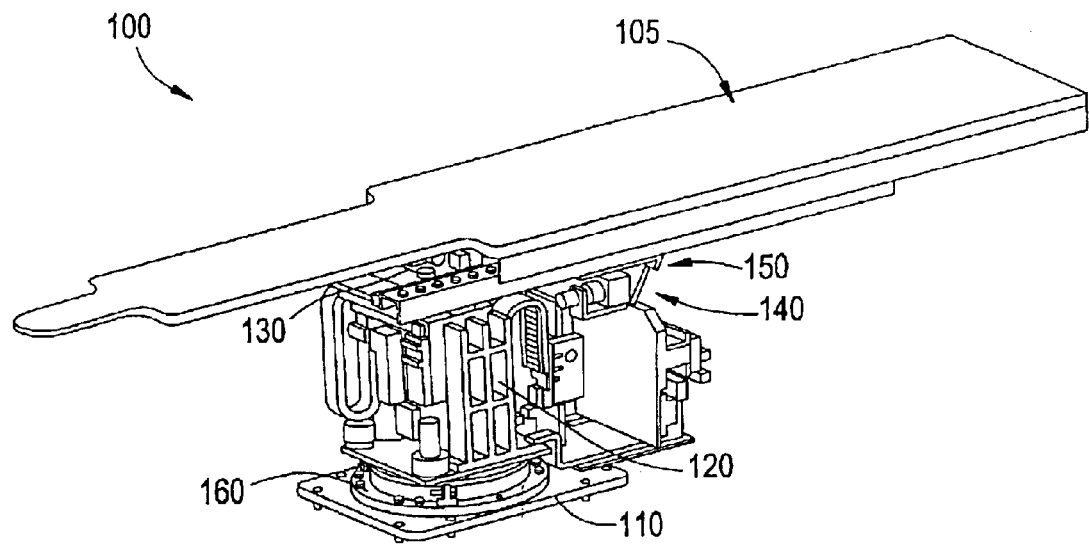
FIG. 1 illustrates a patient positioning system that is used in accordance with an embodiment of the present invention.
Figure 1:
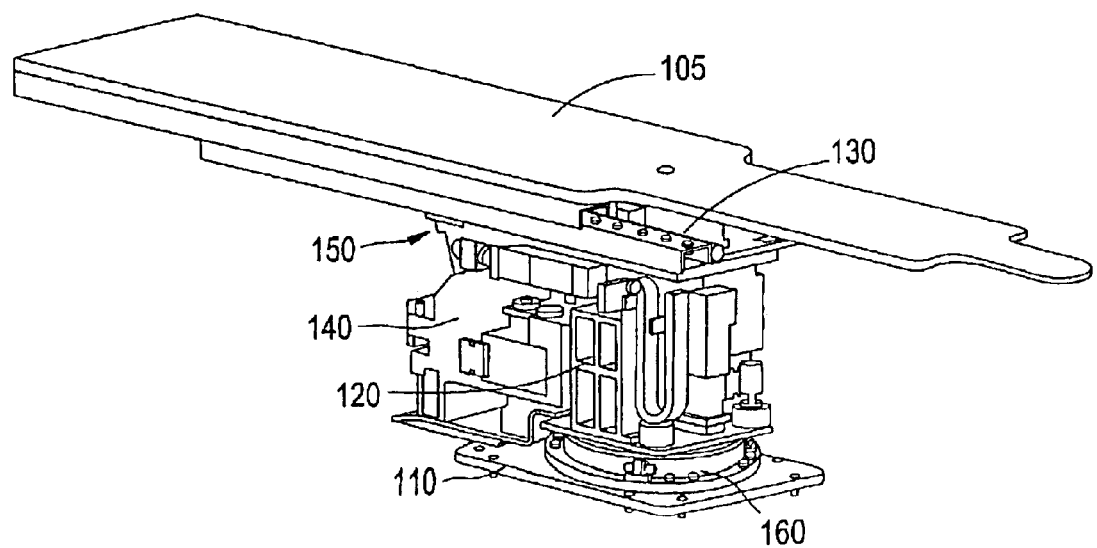

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a patient positioning system 100 that is used in accordance with an embodiment of the present invention. The patient positioning system 100 includes a patient positioning surface 105, a base 110, a telescopic lift system 120, a longitudinal system 130, a tilt system 140, a lateral system 150 and a rotation system 160. The patient positioning system 100 is grouted, or fixed to the floor at the table base 110. The system 100 also includes a motion control system 170 (not pictured). The patient positioning system is described in more detail in U.S. patent application entitled "Grouted Tilting Patient Positioning Table for Vascular Applications," application Ser. No. 10/065,866, filed on Nov. 26, 2002, with inventors Muthuvelan Varadharajulu, Rajagopal Narayanasamy, Baskar Somasundaram, and Shaji Alakkat. The application is herein incorporated by reference including the specification, drawings, claims, abstract, and the like. Additionally, the following U.S. patent applications are also incorporated by reference: "Method and Apparatus for Collision Avoidance in a Patient Positioning Platform," Ser. No. 60/429,283, Application No. 10/248,759, filed on Feb. 25, 2003, with inventor Muthuvelan Varadharajulu; "Multiconfiguration Braking System," Ser. No. 60/10/379, 122, filed on Mar. 4, 2003, with inventor Baskar Somasundaram; and "Method and Apparatus for Tilting in a Patient Positioning System," Ser. No. 10/379,124, filed on Mar. 4, 2003, with inventor Shaji Alakkat.

Figure 2:
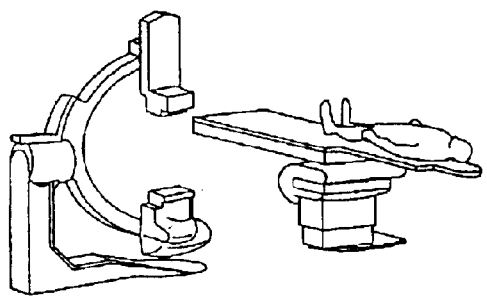
FIG. 2 illustrates positions of a patient positioning surface used in accordance with an embodiment of the present invention.
Figure 2:
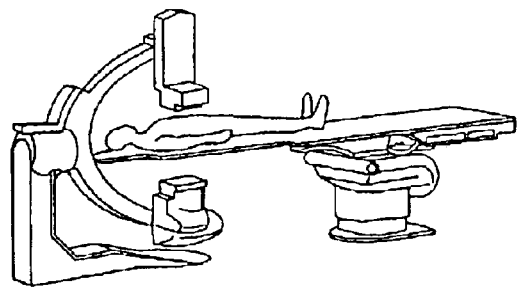
Figure 2:
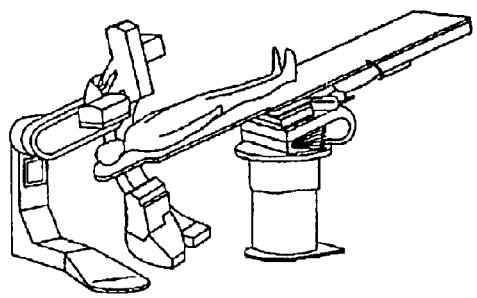
Figure 2:
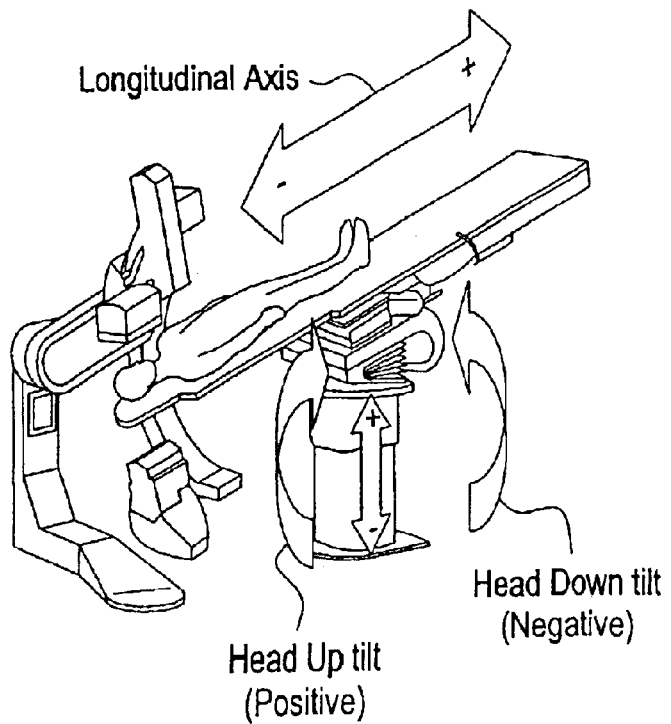
Figure 3:
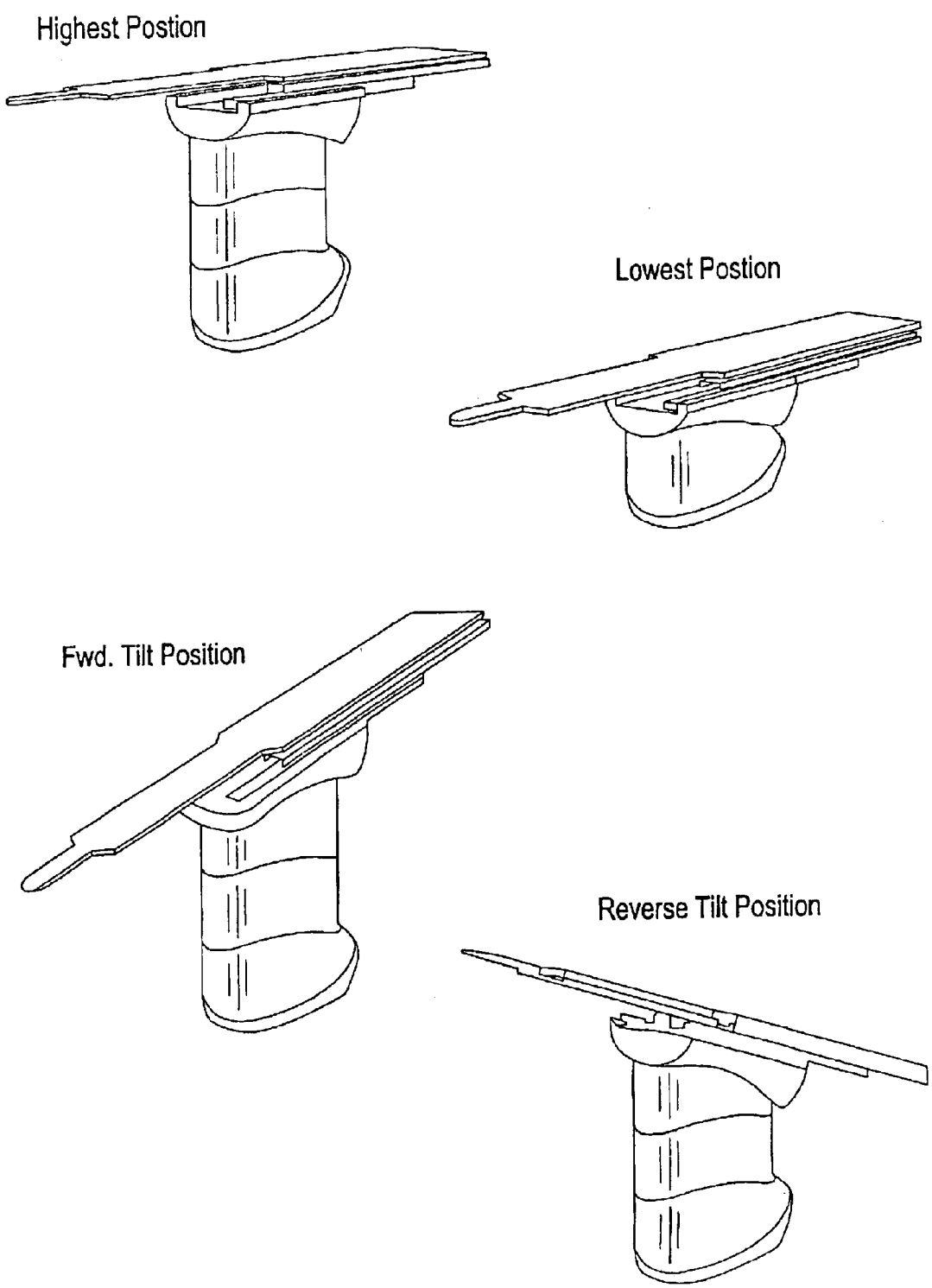
FIG. 3 illustrates positions of a patient positioning surface used in accordance with an embodiment of the present invention.

To enhance loading and unloading of a patient, the patient positioning surface 105 may rotate around a vertical axis using the rotation system 160. The patient positioning surface 105 may also be manually rotated about the rotation system 160. To move the patient to an image area, the patient positioning surface 105 may move vertically using the telescopic lift system 120 from a height at which the patient may be conveniently loaded to a height where imaging may occur (780 mm to 1080 mm, for example). To move a portion of the patient's body into the image area, the patient positioning surface 105 may move in a lateral direction (+/−140 mm from a normal imaging position, for example) using the lateral system 150. FIGS. 2 and 3 illustrate exemplary positions of the patient positioning surface 105 used in accordance with certain embodiments of the present invention.

Figure 4:
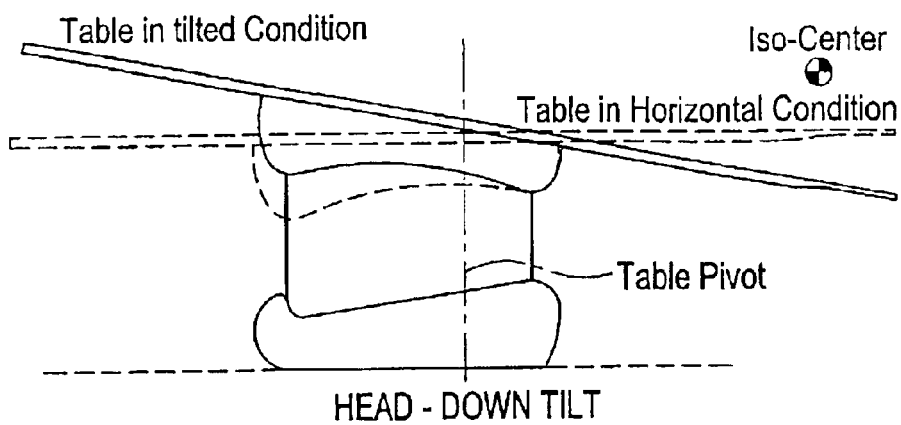
FIG. 4 depicts a tilting of a patient positioning surface with and without iso-center tracking used in accordance with an embodiment of the present invention.
Figure 4:
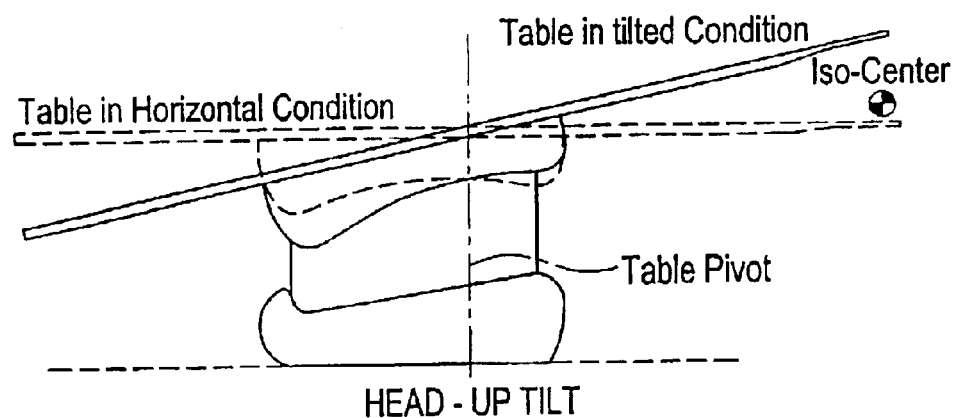
Figure 4:
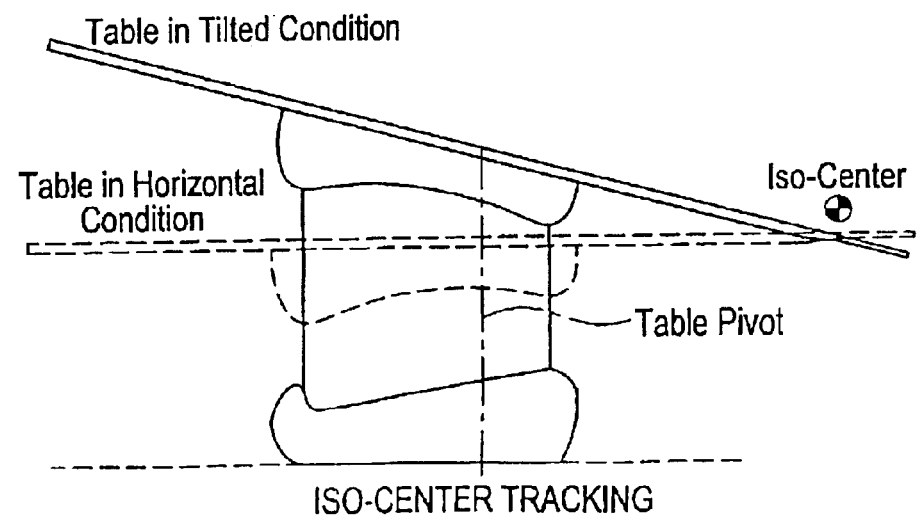

Additionally, the telescopic lift system 120 may provide a stroke or lift motion for iso-center tracking. An iso-center is the point at which three axes of an x-ray imaging system gantry meet (not shown). Iso-center tracking maintains a patient region of interest at the iso-center during tilt or other movement of the patient positioning system 100. Additional stroke for iso-center tracking is provided by the telescopic lift system 120 supported by a telescopic guide mechanism to accommodate a moment resulting from overhanging load. FIG. 4 depicts a tilting of the patient positioning surface 105 with and without iso-center tracking used in accordance with an embodiment of the present invention.

For head to toe coverage of the patient, the patient positioning system 100 may use longitudinal motion from the longitudinal system 130. For bolus chasing (following a bolus or contrast agent through a patient's blood vessels), the longitudinal motion may be motorized with a variable speed motor (2 to 15 cm/sec, for example) using the longitudinal system 130 and a guide mechanism. In a certain embodiment, in addition to motorized motion, lateral and longitudinal axes include a clutch to support manual panning of the patient positioning surface 105. That is, the clutch may be released to allow the patient positioning surface 105 to be positioned manually by an operator.

For emerging vascular procedures, such as emergent situations (falling artery pressure, for example), venous access and $CO_2$ studies, the patient positioning surface 105 may tilt head up and head down in the longitudinal direction (12 degrees up and 20 degrees down, for example). A region of interest of the patient may remain at the iso-center or the image area when the patient positioning surface 105 is tilted. In an embodiment, the region of interest remains in the iso-center or the image area using synchronized motion of the telescopic lift system 120, the longitudinal system 130 and the tilt system 140 as defined by the Inverse Kinematics Formula.

In an embodiment, mechanical and electrical interlocks and position feedback from the patient positioning system 100 help to ensure patient safety. Patient restraints may be provided to keep the patient on the patient positioning surface 105 and to help ensure patient safety. Certain embodiments of the patient positioning system 100 help to ensure a high level of patient safety through effective safety interlock systems and redundant systems for avoiding single point failures.

Safety interlocks and redundant safety systems are provided to help ensure patient safety in the patient positioning system 100. In an embodiment, all axes in the patient positioning system 100 are designed to have position encoders to read the coordinates of the patient positioning surface 105 at any position at any time. Ground clearance of the patient positioning surface 105 is calculated, and motion of the patient positioning surface 105 stops if the ground clearance is less than or equal to a specified safe limit. Thus, collisions may be avoided.

In a certain embodiment, all axes are designed with redundant safety systems to avoid single point failures and to help ensure patient safety. Each motorized axis of the patient positioning system 100 may include an incremental encoder and brake (on the drive or motor side). Each motorized axis may also include an absolute encoder and brake at the load side. During normal operation, the brake at the drive side operates to stop any axis of motion. If a problem arises in the driveline, a difference in incremental encoder (drive side) and absolute encoder (load side) readings operates the brake at the load side to stop the axis.

Additionally, both power-on and power-off brakes may be activated during procedures to ensure stability and rigidity of the patient positioning surface 105. During power-off conditions, only the power-off brake may be activated to allow easy removal of the patient by rotating the patient positioning surface 105.

The patient positioning surface 105 may be prevented from tilting at the lowest position of the patient positioning surface 105, since the lowest position of the patient positioning surface 105 is used for easy loading and unloading of the patient. Each axis is provided with a power-off brake to lock the motion during a power failure and/or any malfunction of the motors and servo drives. Each axis is provided with a software limit, a hardware limit, and mechanical hard stops. An example of a software limit is the following: during normal operations, the patient positioning surface 105 shall not move beyond a certain point. An example of a hard limit is the following: the patient positioning surface 105 is controlled by a limit switch. The limit switch stops the motion of the patient positioning surface 105 if a software malfunction occurs. An example of a mechanical hard stop is as follows: an end stop is provided as backup if both software and hardware limits fail. The coordinates of all axes may be continuously monitored to avoid a collision with the ground and/or predetermined objects.

The following are some examples of operations involving the patient positioning system 100. The examples are provided to illustrate use of components and systems in the patient positioning system 100 and are not intended to be a comprehensive list.

For example, a patient may be loaded on the patient positioning surface 105. First, the patient positioning surface 105 is positioned at 780 mm from the ground using the telescopic lift system 120. Then, the patient positioning surface 105 is rotated to the right-hand or left-hand side using the rotation system 160. Next, the patient is loaded onto the patient positioning surface 105. Patient restraints may be used to secure the patient on the patient positioning surface 105. To unload the patient, the patient positioning surface 105 is rotated to the right-hand or left-hand side using the rotation system 160. The patient positioning surface 105 is repositioned to a height of 780 mm from ground level by the lift system 120. The patient restraints are unlocked, and the patient is removed from the patient positioning surface 105.

Also, for example, the patient may be moved into the image area. First, the rotation system 160 rotates the patient positioning surface 105 to zero degree. Next, the patient positioning surface 105 is moved vertically to the image area using the telescopic lift system 120. Then, the patient positioning surface 105 is adjusted laterally in the image area with the lateral system 150. The patient positioning surface 105 may also be adjusted longitudinally by the longitudinal system 130 to reach a desired position in the image area.

A patient may be positioned on the patient positioning surface 105 for several medical procedures and examinations. For example, in angiography, a patient's height may be adjusted by raising and lowering the patient positioning surface 105 using the telescopic lift system 120. Additionally, four-way panning may be accomplished using the lateral system 150 and the longitudinal system 130. For peripheral angiography, the patient positioning surface 105 may also be rotated into proper position using the rotation system 160 and tilted using the tilt system 140.

For bolus chasing, patient restraints may be used to secure the patient on the patient positioning surface 105. The longitudinal system 130 advances the patient positioning surface 105 in the longitudinal direction in bolus mode (0–15 cm/sec). For venous access and $CO_2$ studies, for example, patient restraints may keep the patient in touch with the patient positioning surface 105, and the lift 120, longitudinal 130, and tilt 140 systems may be used for iso-center tracking to maintain a desired image area during movement. In emergent situations, restraints secure the patient on the patient positioning surface 105, and the tilt system 140 tilts the patient to a desired position.

Cardiac pulmonary resuscitation (CPR) is a procedure performed for patients who suffer from cardiac arrest, for example. In order to bring a patient to a CPR position if the patient positioning surface 105 is in a horizontal position, the patient positioning surface 105 is moved longitudinally in a backward direction using the longitudinal system 130. Then, the patient positioning surface 105 is lowered using the lift system 120. If the patient positioning surface 105 is titled, the tilt system 140 returns the patient positioning surface 105 to a horizontal position. Then, the longitudinal system 130 moves the patient positioning surface 105 backward, and the lift system 120 lowers the patient positioning surface 105 to enable CPR to be performed on the patient.

The telescopic lift system 120 is used by the patient positioning system 100 to accommodate high load, moments, and lift motion or stroke to position a patient in the image area. The tilt system 140 allows the patient positioning system 100 to tilt head up or head down and maintain a desired image through iso-center tracking. The patient positioning system 100 includes a lateral system 150 to move the patient positioning surface 105 laterally using motorized and/or manual panning.

The patient positioning system 100 supports motorized bolus chasing with head to toe coverage so that an image may be traced as the contrast agent travels through the patient. The patient positioning system 100 tracks the coordinates of the patient positioning surface 105. Positioning tracking facilitates collision avoidance with the ground and/or other predetermined objects. Tracking also allows the patient positioning system 100 to return the patient positioning surface 105 to a previously recorded and/or memorized position.

The motion control system 170 for the patient positioning system 100 includes three major parts: a user interface, an I/O board, and servo nodes (not shown). A user may move the patient positioning surface 105 using the user interface. User interface commands are processed by the I/O board (CPU). Commands are then sent to corresponding servo nodes that control the respective axis movements. In an embodiment, a Power PC-based micro controller is used as the CPU. An application program, which is running on a real-time operating system, may control the patient positioning system 100.

Clearance between the patient positioning surface 105 and the ground and/or another object is determined dynamically based on the positions of the lift, longitudinal, and tilt axes in the patient positioning system 100. The motion control system 170 may store a safe clearance value. The motion control system 170 determines the clearance between the patient positioning surface 105 and the ground or another object. The motion control system 170 compares the measured clearance and the safe clearance value. The motion control system 170 stops movement of axes of the patient positioning system 100 if the measured clearance is less than or equal to the stored safe clearance.

Figure 5:
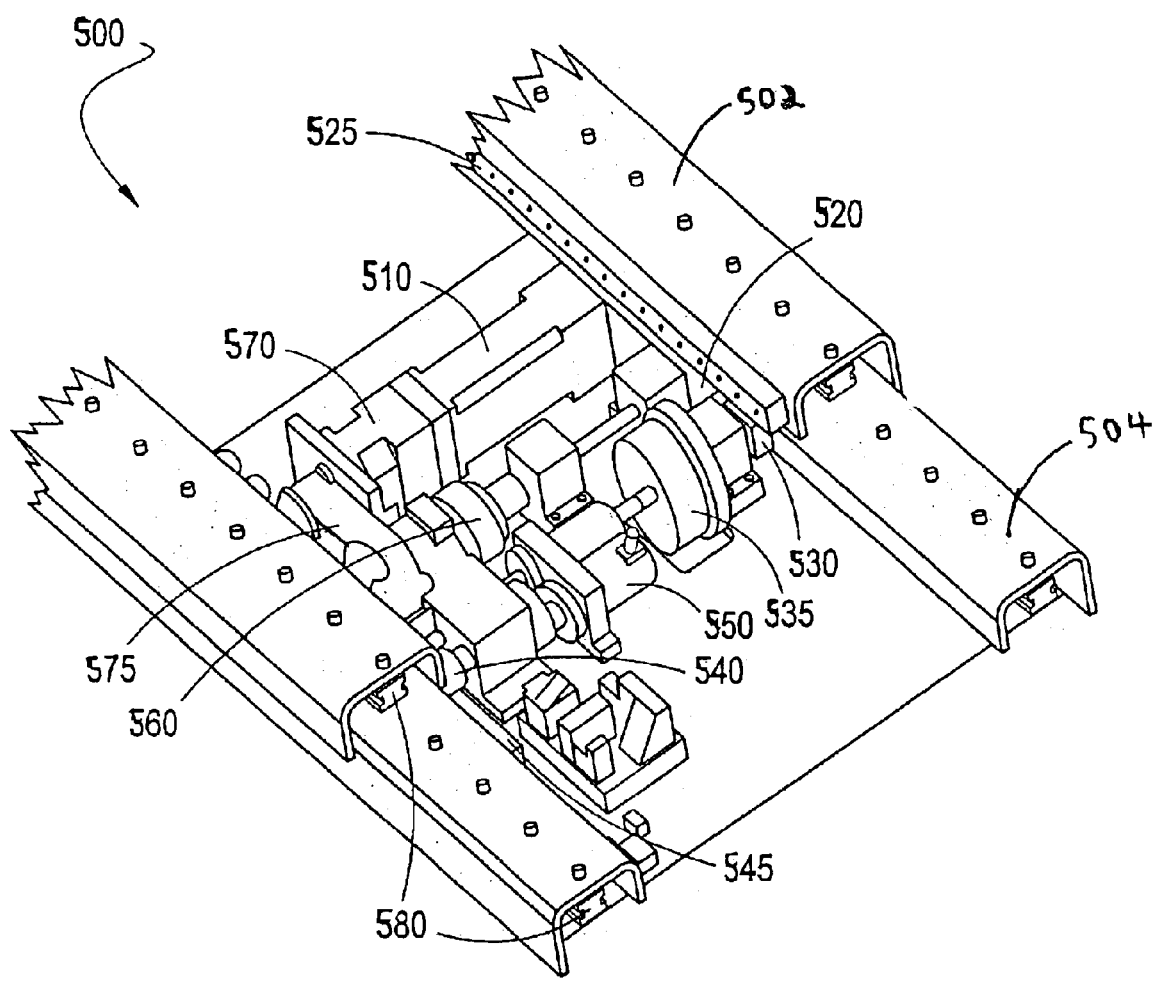
FIG. 5 illustrates a synchronization drive for a longitudinal axis telescopic guidance mechanism used in accordance with an embodiment of the present invention.
Figure 6:
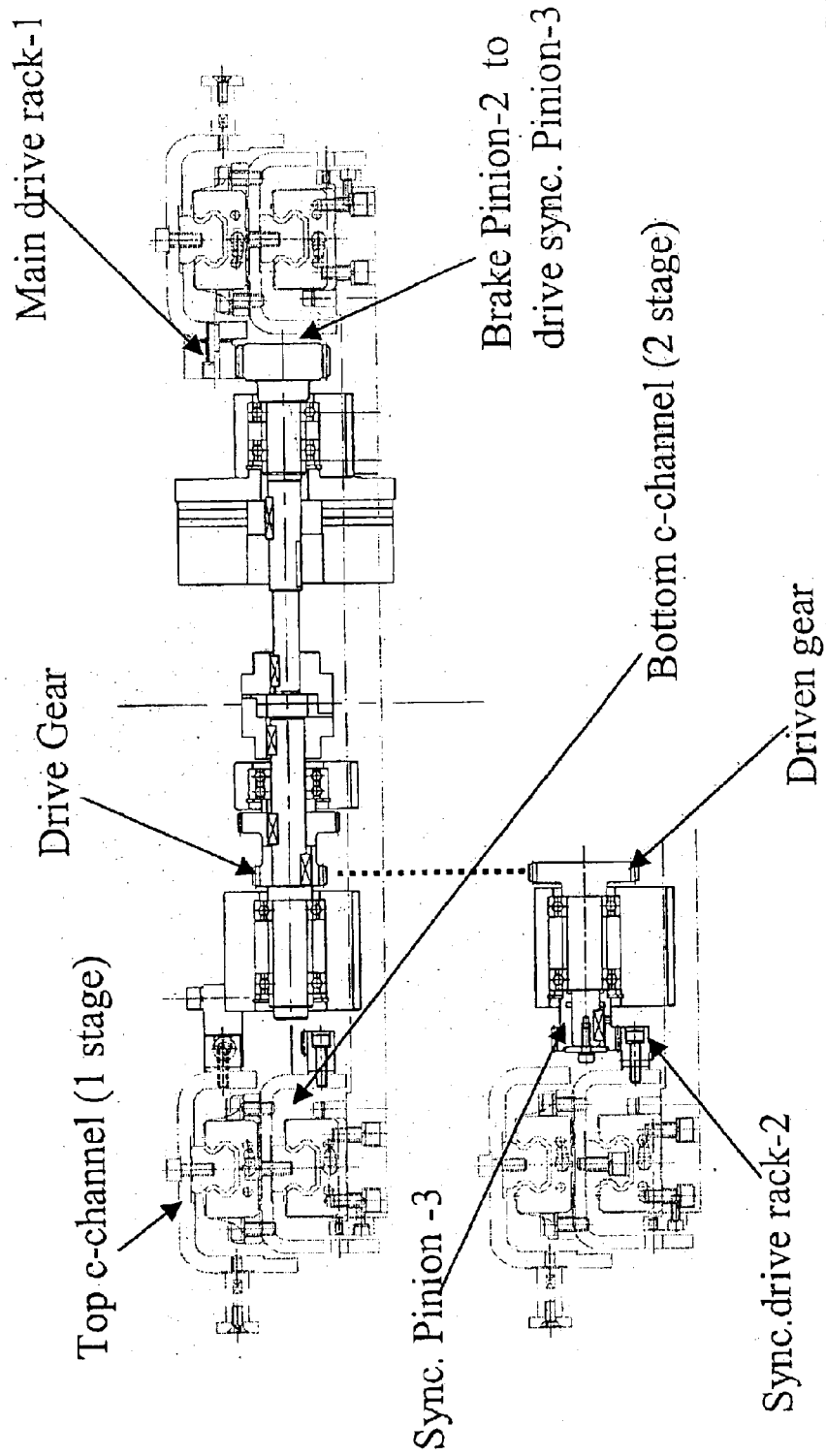
FIG. 6 illustrates a synchronization drive for a longitudinal axis telescopic guidance mechanism used in accordance with an embodiment of the present invention.

FIG. 5 illustrates a synchronization drive for a longitudinal guidance system 500 used in accordance with an embodiment of the present invention. The longitudinal system 500 is similar to the longitudinal system 130 described above in relation to FIG. 1 and the patient positioning system 100. The patient positioning system 100 allows longitudinal motion for imaging in the forward direction (1700 mm, for example). For iso-center tracking during tilting of the patient positioning surface 105, the patient positioning surface 105 may move longitudinally in the reverse direction (25 mm, for example). FIG. 6 illustrates another view of a synchronization drive for a longitudinal guidance system 500 used in accordance with an embodiment of the present invention.

Longitudinal motion is produced by the longitudinal system 500. The longitudinal system 500 includes two-stage telescopic rails with LM guides 580. Motion is produced by a timing belt 575 that is driven by a motor 510 and guided by the LM guides 580. Longitudinal motion is produced through a rack and pinion mechanism driven by the motor 510. Motion of the two telescopic rails is synchronized through an additional rack and pinion mechanism. The longitudinal system 500 also includes a clutch 560 that disengages the motor 510 of the longitudinal system 500 from drive to aid in manual panning of the patient positioning surface 105. An absolute encoder 550 is used to determine the position of the patient positioning surface 105 in the longitudinal direction.

The two-stage telescopic longitudinal system 500 is divided into a top stage 502 and a bottom stage 504. The motor 510 drives the top section. The top and bottom stages 502, 504 are synchronized to aid in low and uniform panning of the patient positioning surface 105 and to help avoid slippage of the bottom section during tilt of the patient positioning surface 105.

The first stage 502, or top c-channel, of the telescopic longitudinal system 400 is driven by a main drive pinion 520 and a main rack 525 through the motor 510. The main rack 525 drives the brake pinion 530 of the brake axis 535. The drive from the brake pinion 530 is transmitted to a synchronization pinion 540 through a drive gear and a driven gear. The drive and driven gear from a gearbox 570 determine the direction of movement of a synchronization rack 545. The synchronization pinion 540 drives the synchronization rack 545, which is mounted on to the second stage 504, or bottom c-channel, of the telescopic longitudinal system 500. The relative motion and mechanical advantage for manual panning are achieved by the gear ratio of the brake pinion 530 and synchronization pinion 540.

The synchronization rack 545 receives drive from the main rack 525. In an embodiment, the gear ratio between the pinions 520, 530, and 540 is designed such that the synchronization rack 545 moves 800 m when the main rack 525 moves 1700 mm, for example. If both of the racks 525, 545 engage with the pinions 520, 530, and 540 and are tied together by the drive elements, free movement of the patient positioning surface 105 is minimized.

Resistance for manual panning results from friction in linear motion blocks with the linear motion guides 580 of the guidance system 500. Manual movement of the top c-channel 502 is transferred to the bottom c-channel 504 through the synchronization mechanism. In an embodiment, the size of the brake pinion 530 meshing with the main rack 525 is half the size of the synchronization pinion 540 meshing with the bottom c-channel 504. As a result, the effort to move the bottom c-channel 504 or second stage may be reduced by half, for example. The top c-channel 502 is supported throughout the stroke. Overhang of the top c-channel 502 is reduced because the bottom c-channel 504 moves along the top c-channel 502. The reduced overhang of the top c-channel 502 reduces a bending moment and reaction forces on the linear motion blocks with the linear motion guides 580. Manual panning may be more uniform and have easier movement.

Figure 7:
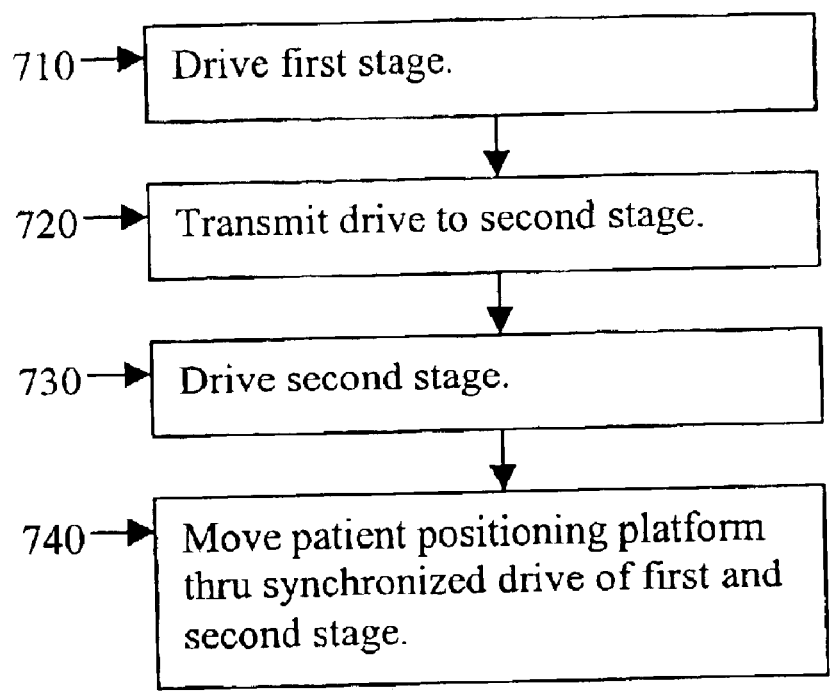
FIG. 7 illustrates a flow diagram for longitudinal telescopic guidance of a patient positioning platform using a synchronization drive in accordance with an embodiment of the present invention.

FIG. 7 illustrates a flow diagram 700 for longitudinal telescopic guidance of a patient positioning platform using a synchronization drive in accordance with an embodiment of the present invention. First, at step 710, the first stage 502 is driven. For example, a gear and drive system drives the first stage 502. Next, at step 720, a rack and pinion system transmits the drive from the first stage 502 to the second stage 504. That is motion generated in the first stage 502 by the gear system is transferred to the second stage 504 via a system of racks and pinions. Then, at step 730, the second stage 504 is driven. Thus, for example, the first stage 502 is moved and that movement is transmitted from the first stage 502 to the second stage 504 via a rack and pinion drive system. At step 740, the patient positioning platform is moved in a longitudinal direction using drive from the synchronized first and second stages.

Thus, certain embodiments of the present invention utilize a rack and pinion arrangement for both the first stage 502 and the second stage 504 of a telescopic guidance mechanism 500. No direct drive is applied to the synchronization rack 545 of the second stage 504. Drive is produced in the main rack 525 of the first stage 502. Synchronization is maintained during both motorized motion and manual movement. Using gear ratios between the two stages of rack and pinion drives to maintain relative position and to reduce panning effort for the patient positioning surface 105.

Certain embodiments of the present invention minimize shocks or jerks to the patient since relative motion of the telescopic guidance system 500 is maintained through full stroke of the patient positioning surface 105. Certain embodiments result in increased safety in longitudinal motion of the patient positioning surface 105 in a tilted condition since free movement of the second stage 504 is minimized. A more uniform panning effort throughout the stroke of the patient positioning surface 105 may be achieved since the second stage 504 moves in synchronization with the first stage 502. Positive synchronization of the drive system through rack and pinion minimizes the possibility of slippage between stages.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A patient positioning system for medical applications, said system comprising:

a patient positioning surface for supporting a patient;

a lift subsystem for adjusting elevation of said patient positioning surface;

a longitudinal subsystem for moving said patient positioning surface in a longitudinal direction, said longitudinal system including a first stage and a second stage, wherein said second stage is driven in synchronization with said first stage to move said patient positioning surface in a longitudinal direction;

a tilt subsystem for tilting said patient positioning surface;

a position sensor for determining a position of said patient positioning surface; and a control subsystem for controlling operation of said patient positioning system.

2. The system of claim 1, further comprising a lateral subsystem for moving said patient positioning surface in a lateral direction.

3. The system of claim 1, further comprising a rotation subsystem for rotating said patient positioning surface.

4. The system of claim 1, further comprising at least one brake to halt motion of said patient positioning surface.

5. The system of claim 1, wherein said longitudinal system further comprises a rack and pinion system to drive said first and second stage.

6. The system of claim 1, wherein gear ratios are used between rack and pinion drives for said first and second stages to position said patient positioning surface.

7. The system of claim 1, wherein said longitudinal system allows manual movement of said patient positioning surface.

8. The system of claim 1, wherein said control system performs iso-center tracking to maintain a region of interest of said patient in an image area during tilt.

9. The system of claim 1, wherein said position sensor comprises at least one encoder.

10. A method for synchronized longitudinal guidance of a patient positioning platform, said method comprising:

driving a first stage;

transmitting drive from said first stage to a second stage through a first pinion and a second pinion each contacting a rack connected to said first stage; and moving a patient positioning platform in a longitudinal direction using drive from said synchronized first stage and second stage.

11. The method of claim 10, wherein a gear and drive system drives said first stage.

12. The method of claim 10, wherein a rack and pinion system transmits drive from said first stage to said second stage.

13. The method of claim 10, further comprising moving said patient positioning surface to a desired position.

14. The method of claim 10, further comprising measuring said current position of said patient positioning surface using a position sensor.

15. The method of claim 10, further comprising adjusting gear ratios between rack and pinion systems of said first stage and said second stage to position said patient positioning surface.

16. A synchronization drive system for a longitudinal axis telescopic guidance mechanism, said system comprising:

a top channel driven by a motor;

a bottom channel synchronized with said top channel said bottom channel driven by said top channel; and a rack connected to said top channel and a plurality of pinions for transmitting drive from said top channel to said bottom channel, said plurality of pinions including a first pinion and a second pinion each contacting said rack.

17. The system of claim 16, further comprising a gear for transmitting drive from said top channel to said bottom channel using said rack and pinions.

18. The system of claim 16, further comprising a plurality of racks and pinion for transmitting drive from said top channel to said bottom channel.

19. The system of claim 16, wherein the size of said first pinion meshing with said rack is half the size of a third pinion meshing with a second rack, said second rack connected to said bottom channel.

20. The system of claim 16, wherein said bottom channel moves along said top channel.

* * * * *

UNITED STATES PATENT AND TRADEMARK OFFICE
CERTIFICATE OF CORRECTION

PATENT NO. : 6,857,147 B2
DATED : February 22, 2005
INVENTOR(S) : Somasundaram

It is certified that error appears in the above-identified patent and that said Letters Patent is hereby corrected as shown below:

Column 9,
Line 22, delete "stage" and substitute therefore -- stages --.

Column 10,
Line 20, after the words "with said top channel" insert -- , --.

Signed and Sealed this

Twenty-third Day of August, 2005

JON W. DUDAS
*Director of the United States Patent and Trademark Office*